United States Patent [19]

Powell

[11] Patent Number: 5,641,901

[45] Date of Patent: Jun. 24, 1997

[54] ASPHALT CONCRETE SAMPLE RUTTING MACHINE

[76] Inventor: Raymond Powell, 6 Calhoun Rd., Montgomery, Ala. 36109

[21] Appl. No.: 554,004

[22] Filed: Nov. 6, 1995

[51] Int. Cl.[6] .................................................. E01C 23/01
[52] U.S. Cl. .................................. 73/146; 73/8; 73/865.6
[58] Field of Search ................................ 73/8, 146, 865.6

[56] References Cited

U.S. PATENT DOCUMENTS

| | | | |
|---|---|---|---|
| 3,444,727 | 5/1969 | Bourdin et al. | 73/146 |
| 4,887,463 | 12/1989 | Wood | 73/146 |

*Primary Examiner*—Elizabeth L. Dougherty
*Assistant Examiner*—Joseph L. Felber

[57] ABSTRACT

The disclosed machine is comprised of a chassis, process control box and load wheel assembly. The chassis is designed to attach to commercially available controlled temperature heating baths. The primary functions of the process control box are to distribute electrical power, monitor sensor responses to electrical inputs, and to control the overall operation of the load wheel assembly. The load wheel assembly applies multiple load applications while not rolling off the surface of a standard asphalt concrete specimen.

1 Claim, 6 Drawing Sheets

ASPHALT CONCRETE SAMPLE RUTTING MACHINE

BACKGROUND OF THE INVENTION

1. Field

This invention is directed generally to asphalt concrete performance testing equipment and in particular to those devices that attempt to predict the resistance of a designed asphalt concrete mixture to permanent plastic deformation, commonly referred to as rutting.

Asphalt concrete is the most common type of pavement surface material used in the United States. Due to the large investments most states have in asphalt pavements, it follows that they expend a significant amount of resources optimizing mix designs to achieve superior products. To facilitate the design process, different parts of the country design asphalt concretes to resist the types of failures that they most frequently encounter. Consequently, in warmer climates a major design consideration is the resistance a designed mix will have to rutting. It is cost effective to test designed mixes before they are placed to obtain information that will aid the engineer in predicting how they will perform after they are in service. Decades of research have yielded several pieces of equipment that test laboratory samples in the hope of predicting the tendency a designed mix will have to experience permanent plastic deformation while in service.

1. Description of the Prior Art

Equipment recently developed attempts to quantify the rutting susceptibility of asphalt concrete mixes. Loosely based on a European design, currently utilized laboratory equipment consists of an environmental chamber and a load beam. While a test specimen is environmentally conditioned to a temperature that approximates a maximum service condition, a loaded wheel rolls back and forth along a stationary beam. Each time the wheel passes over the sample, a load repetition is applied. As many loads are applied, the sample experiences permanent plastic deformation. Test results reflect the magnitude of the measured rut following a fixed number of load repetitions. The primary difference between the American and European devices is that the American device uses an inflated tube between the wheel and the sample to control contact pressure.

The equipment currently in use is limited in a number of ways. The most notable drawback is the applicability of test results. There is considerable debate regarding the performance similarities between a specially prepared laboratory sample and an in-place roadway pavement. Some feel that it is impossible to compact the small rectangular samples in a laboratory environment in such a way that they actually represent the mix as designed and constructed with respect to such parameters as confining stress, density and void ratio.

Critics of the current process note that simulations at temperatures that are representative of actual summertime service temperatures cannot be run without experiencing premature failures as evidence to support this position. Additionally, the special equipment that is required can make the process financially prohibitive.

Further, excessive time may be required to conduct the test as the load wheel must change direction between each application. For samples that are designed to be rut resistant, a successful proof test may take many hours to complete. This limitation would hinder the use of such devices for field quality control, where additional test time may mean that a significant amount of inferior pavement has been placed.

The above mentioned equipment, while providing a method for approximating the rutting susceptibility of an asphalt, leaves substantial room for improvement, For examples a machine that could utilize the standard design specimens (see AASHTO T 245) would avoid the question of similarity between rutted samples and constructed pavements. Also, the problem of confining stress could be completely avoided if there were a way to test the specimen without extracting it from its compaction mold. Consequently, existing compaction equipment could be utilized to prepare the test specimens, thereby avoiding the cost of new compaction equipment entirely, Further, use of existing environmental conditioning equipment would make a rut testing device more attractive for industry-wide use. Due to the size of today's standard samples and existing equipment, however, a radically different approach to the method of applying the load repetition has to be considered.

SUMMARY OF THE INVENTION

The primary objective of the present invention is to provide a means of utilizing conventional compaction and temperature conditioning equipment to add a dimension of cost effectiveness to current methodology. Rather than using a wheel and beam configuration that requires special compaction and environmental control, a radical new load wheel has been designed and incorporated that allows the standard compaction specimen to be rut tested while the specimen is suspended within a common temperature bath. The load wheel assembly does not try to run off the sample because the design utilizes ten smaller wheels that are free-spinning.

Because the new device does not require the wheel to apply the load, decelerate, stop and reverse motions testing may be conducted in a relatively short period of time as several loads may be applied per second. Additional advantages of the present invention will be apparent after review of the figures included herein.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

Figure 1:
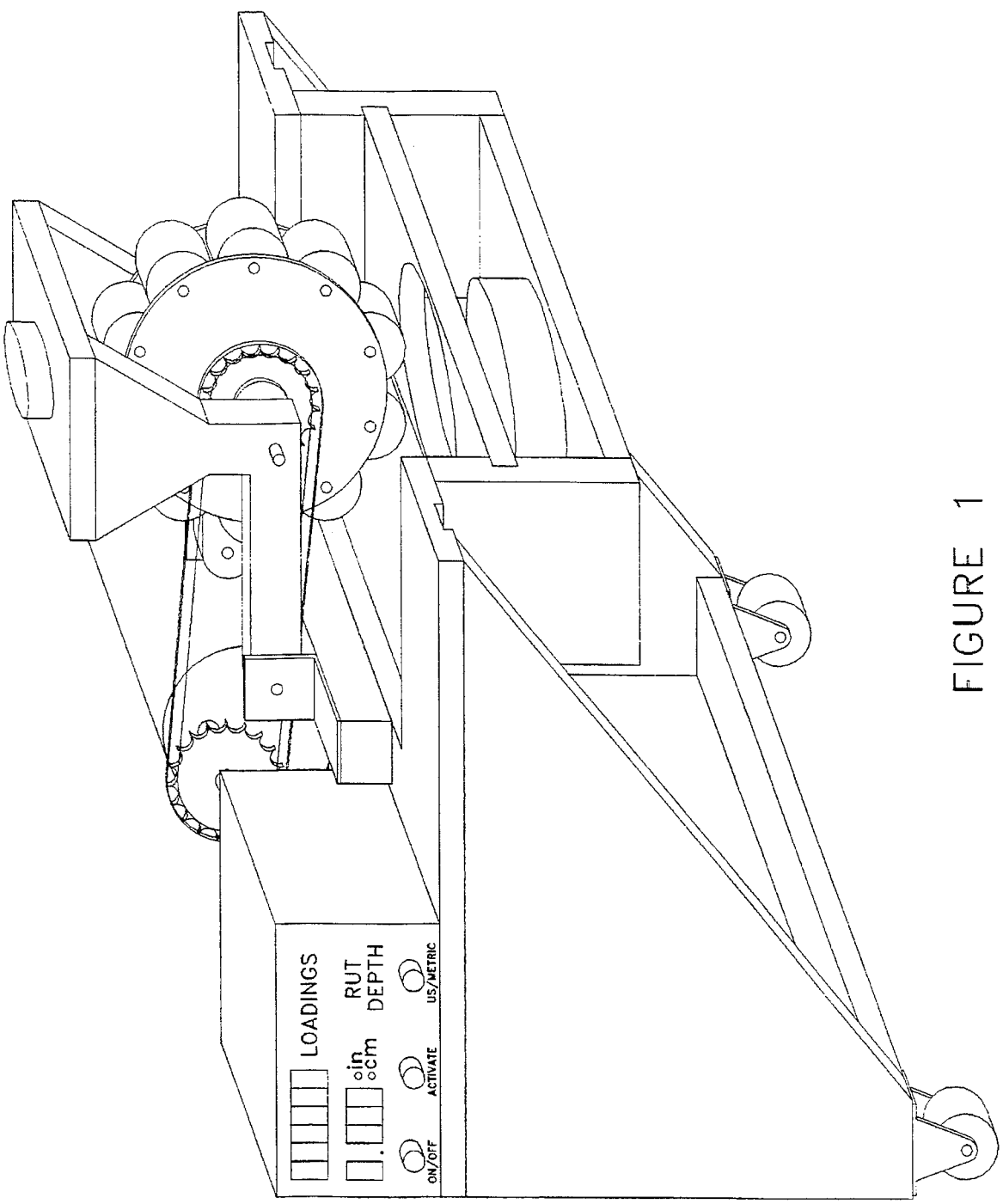
FIG. 1 is a perspective view of the invention, which the inventor intends to call the RUTMETER as seen free standing, without part numbers and not attached to a common temperature bath.

The present invention may be embodied in other specific forms without departing from the spirit or essential attributes thereof and, accordingly, reference should be made to the following claims rather than the above described specifications or drawings as indicating the scope of the invention.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
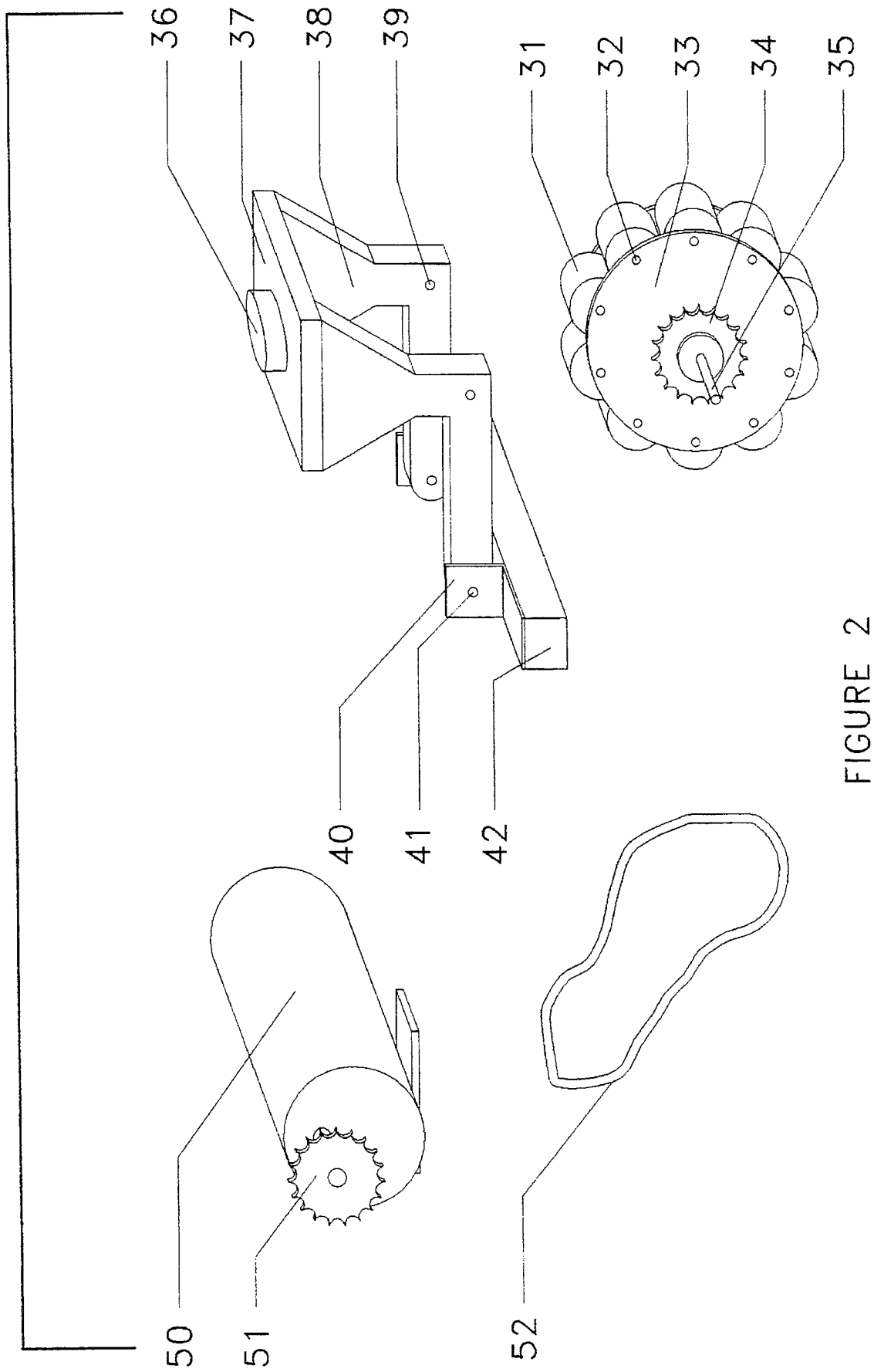
FIG. 2 is a perspective view of the load application wheel comprising a portion of FIG. 1.

Referring to FIG. 1, there is illustrated a RUTMETER drawn to scale that incorporates the lead wheel assembly, process control box, and chassis as components of this application. The lead wheel assembly consists of those numbered parts in FIG. 2 where the obvious departure from prior art is seen in part numbers 31 through 35 that comprise the lead wheel itself. Rather than incorporating a single conventional wheel that travels back and forth across the top of a laboratory prepared specimen, FIG. 2 illustrates a series of free, spinning smaller wheels 31 that are mounted at 36 degree intervals via axle bolts 32 to two plates 33 so that tile entire assembly may spin in place while remaining in the same horizontal position on the top of a laboratory prepared specimen. The plates 33 are mounted to an axle 35 that is set in motion by a chain driven sprocket 34. The axle 35 attaches through guide holes 39 on either side to the travel arms 38 that are connected on their upper portion by a lead platform 37. A weight guide 36 sits atop the load platform to ensure that any donut weights added to apply a vertical lead do not slip off while The device is in motion. The pivot arms 38 that enable free near-vertical translation of the lead wheel are attached to a mounting bar 42 via guide holes 41 that are bolt-connected to angles 40 on either side. A commercially available gear motor 50 turns a sprocket 51 that sets the stationary lead wheel in circular motion via a chain 52.

Figure 3:
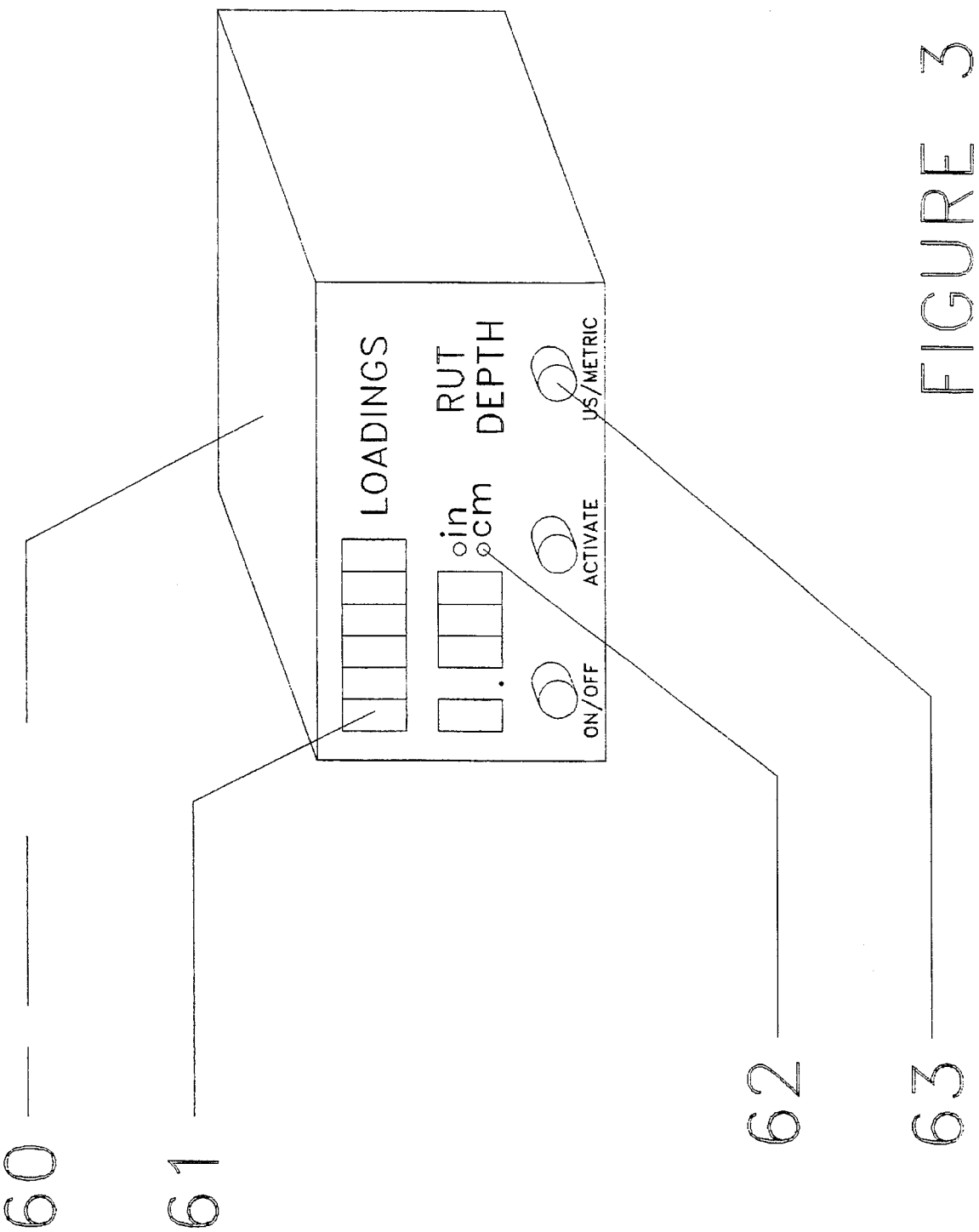
FIG. 3 is a perspective view of the process control box comprising a portion of FIG. 1.

The process control box shown in FIG. 3 of the preferred embodiment contains basic information needed to successfully document the response of laboratory prepared asphalt concrete samples subjected to repetitive loadings by the aforementioned lead wheel assembly (31, 32, 33, 34, 35). Electronics required to monitor the output of any attached displacement sensors are housed in a protective enclosure 60 that also serves as the permanent mounting location of LCD panels 61 on which data such as total number of loadings and displacement may be displayed. Displacement sensors of this nature are selected from commercial, off-the-shelf components and are chosen at the preference of those users skilled in the art. Single LED's 62 are used to indicate toggle settings that are controlled via button switches 63. As a laboratory prepared sample is loaded repetitively by the rotating, free-spinning wheel with a donut weight on its lead platform 37 above, electronics of the users choice monitor such information as lead count, vertical displacement, etc.

Figure 4:
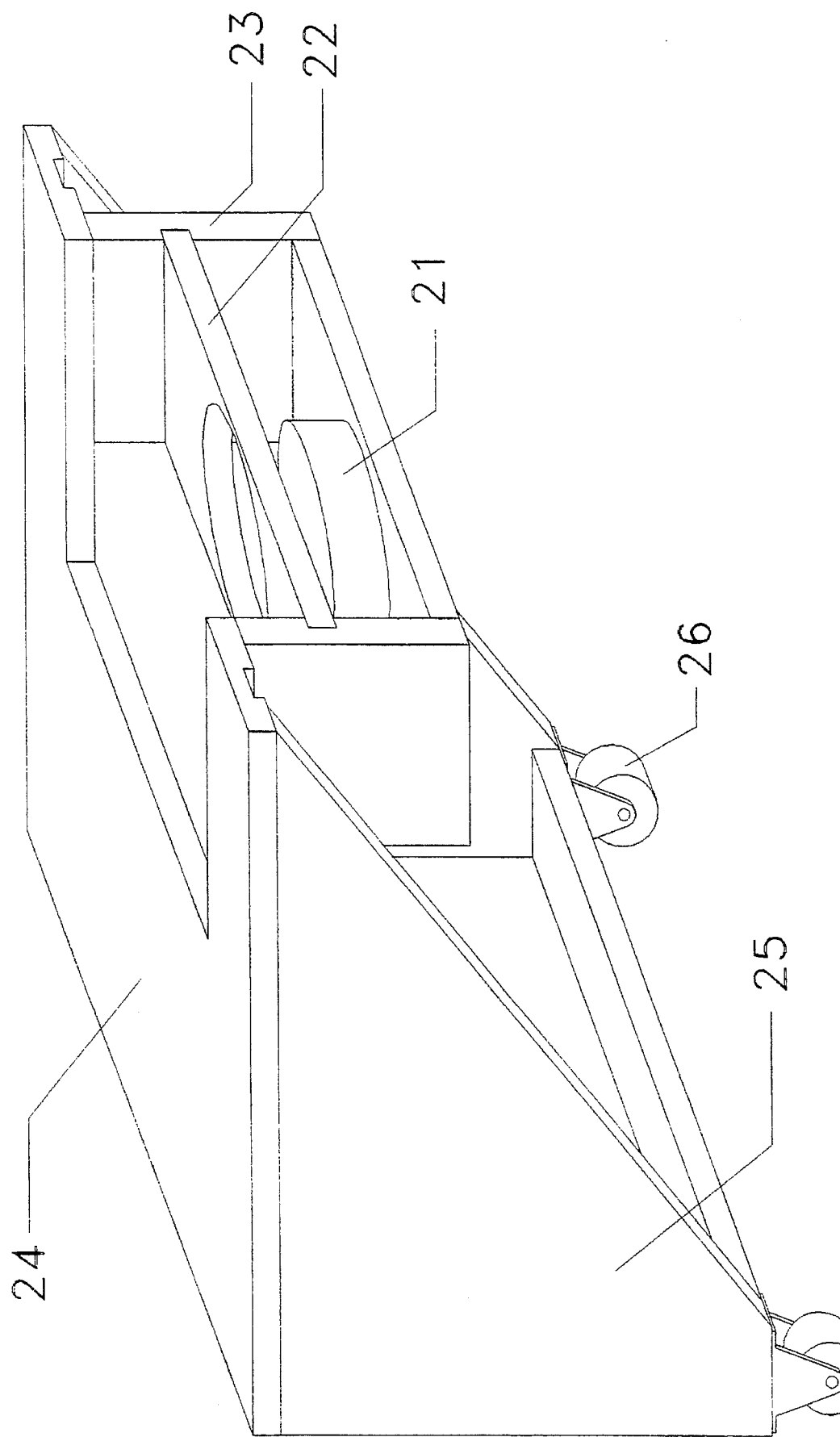
FIG. 4 is a perspective view of tile freestanding chassis comprising a portion of FIG. 1.

FIG. 4 has been included to illustrate the preferred embodiment of the chassis. Here it is seen that a platform 24 supports the motor 50, travel arm mounting bar 42, and process control box 60. The platform 24 has machined grooves on its underside that are placed in such a manner that the top rim of many commonly used asphalt concrete temperature baths fits snugly inside them, thus enabling the chassis to simply "snap" on. In that no upward forces are generated during testing, no additional securing attachments are required. A basket 23 is used to support the laboratory prepared test specimen, which hangs underwater inside a temperature conditioning water bath that is provided separately. The sample is held in place by a shim 21 that fits snugly inside the specimen's compaction mold. As an added measure, an upper brace 22 holds the top of the sample in place as well. Side panels 25 ensure that the chassis will be rigid as the loads are applied thus creating vibration, and dolly wheels 26 have been provided so that the chassis may be easily placed in position over the sample conditioning bath that must be provided separately to facilitate testing.

Figure 5:
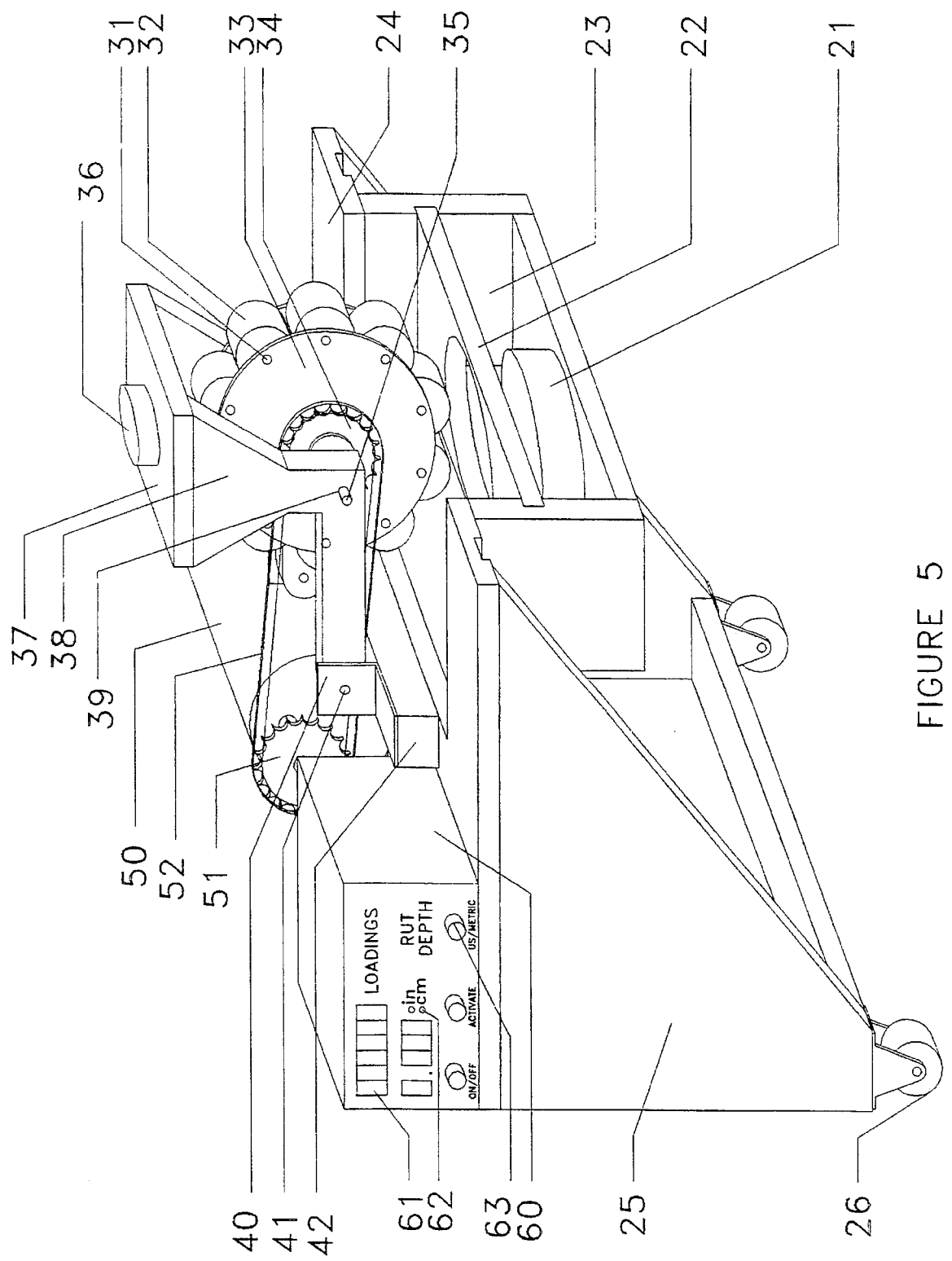
FIG. 5 is a device as shown in FIG. 1 with labeled part numbers.
Figure 6:
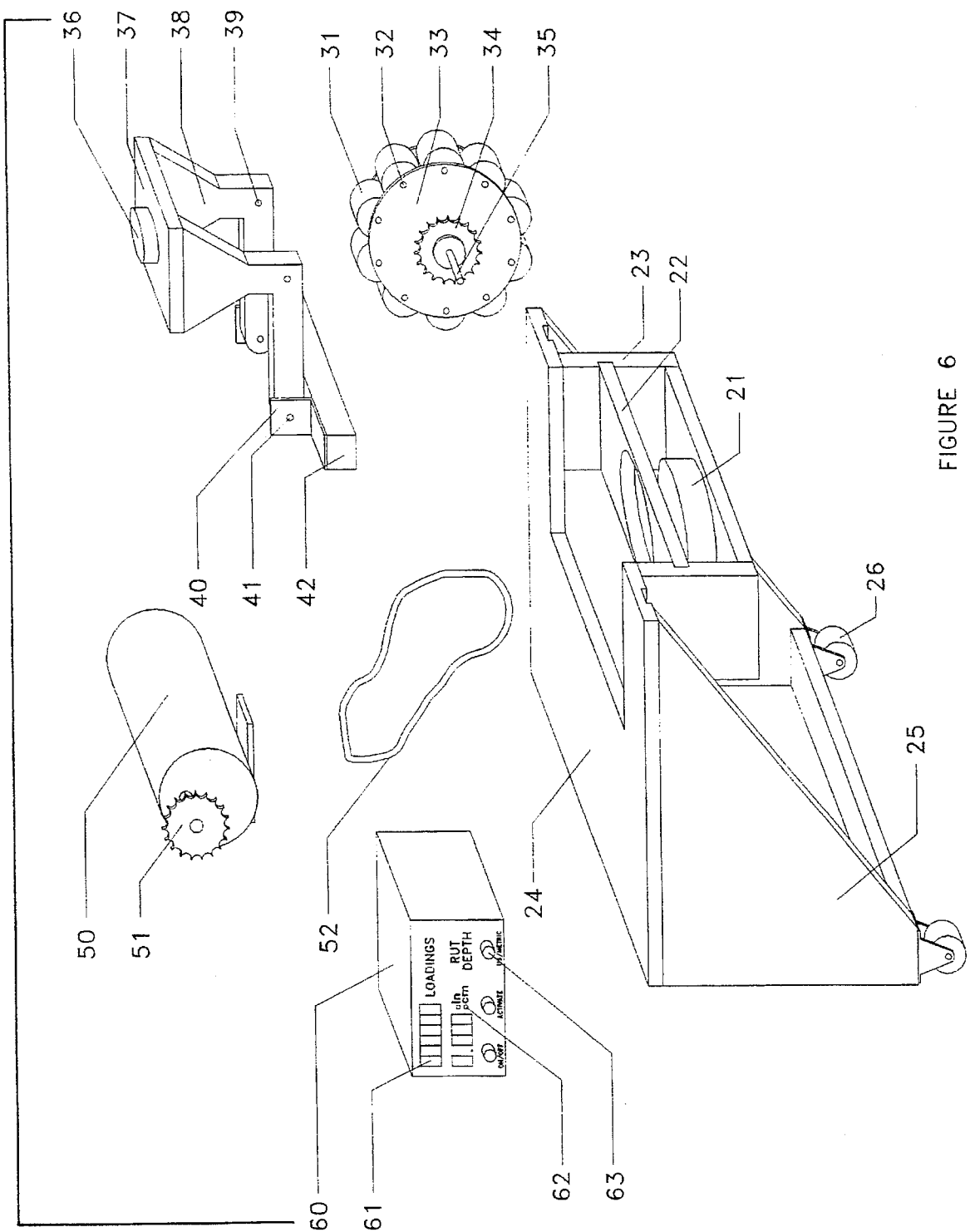
FIG. 6 is an exploded view of FIG 5.

The part labeling system utilized in FIGS. 2 through 4 was superimposed onto FIG. 1 to create FIG. 5 which has been included for clarification purposes. Likewise. FIG. 6 has been included as an exploded view of FIG. 5.

In normal operation, laboratory technicians will prepare asphalt concrete samples as per AASHTO T 245. Instead of jacking the compacted specimens out of their molds, technicians will jack the sample up until its top is approximately flush with the top of the compaction mold. At this time, the specimen and its mold will be inserted into the submerged basket 23 that is underwater when the platform 24 is attached to a conventional water temperature bath (preheated to simulate a maximum summer service temperature for in-place pavements). The shim 21 fits snugly into the bottom of the metal compaction mold to hold it and the sample in place, with the help of the upper brace 22. With the sample now underwater, the load wheel assembly (31, 32, 33, 34, 35) is lowered onto the test surface and a vertical load is applied by stacking a weight onto the load platform 37 via the weight guide 36. The process control box (60, 61, 62, 63) is activated and the commercially available motor 50 sets the load wheel assembly (31, 32, 33, 34, 35) into its spinning motion. Since Ten free-spinning wheels 31 are located along the outer edge of the plates 33, ten separate near-vertical loadings are applied for each revolution to simulate traffic loadings on the final constructed roadway. As load transfer occurs between the smaller wheels 31, the pivot arms 38 translate up and down. While the loads are applied, the process control box counts the number of applications and monitors the cumulative vertical deformation, which is the simulated roadway wheelpath rut. Vertical deformation is monitored by means known to those skilled in the art, which would consist of commercially available off-the-shelf components. By comparing rutting curves for different designed mixes in the laboratory, engineers can determine which asphalt concrete mixes will be less likely to rat under full scale traffic after construction. An item of particular interest to engineers skilled in the art will likely be the number of load applications to induce 0.25 inches of permanent plastic deformation.

It is to be understood that although a small RUTMETER to test laboratory prepared test specimens has been shown, the unique load wheel design of the disclosed invention is equally well suited to test in-place pavements when constructed on a larger scale. Optimum materials and dimensions will depend in part on the intended application.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. An asphalt concrete sample rutting machine comprising a chassis process control box, and load wheel assembly;

wherein said load wheel assembly's main components are ten small wheels that are mounted in thirty-six degree intervals in a circular pattern between two larger circular plates to form a load application wheel;

said load wheel assembly's main components are mounted on bearings to an axle and serve to form a load application mechanism that can rotate in place, thus applying multiple load applications while not rolling off the surface of a standard asphalt concrete specimen; and said load application wheel is attached to the chassis via two hinged travel arms that support a load platform upon which weights may be stacked to control the magnitude of applied loadings, where a sprocket attached to the side of the load application wheel allows it to be set in motion via the use of a low rpm motor and a roller chain.

* * * * *